United States Patent [19]

Luedicke et al.

[11] 4,333,921

[45] Jun. 8, 1982

[54] HAIR CLEANSING CONDITIONER WITH LATHERING ACTION

[75] Inventors: Oscar B. Luedicke, Butler; Thad Domzalski, Pompton Lakes; David Zajac, East Brunswick, all of N.J.

[73] Assignee: American Cyanamid Company, Stamford, Conn.

[21] Appl. No.: 193,217

[22] Filed: Oct. 2, 1980

[51] Int. Cl.³ .............................................. A61K 7/06
[52] U.S. Cl. ...................................................... 424/70
[58] Field of Search ........................................... 424/70

[56] References Cited

U.S. PATENT DOCUMENTS

| | | | |
|---|---|---|---|
| 3,296,145 | 1/1967 | Fendlan et al. | 424/329 |
| 3,449,430 | 6/1969 | Dohr et al. | 424/70 |
| 3,484,523 | 1/1969 | Fendlan et al. | 424/329 |
| 3,496,110 | 2/1970 | Shumway et al. | 424/70 |
| 4,174,296 | 11/1979 | Kass | 424/70 |

OTHER PUBLICATIONS

J. Soc. Cosmetic Chem. vol. 26, pp. 155–168, (1975).

*Primary Examiner*—Donald B. Moyer
*Attorney, Agent, or Firm*—Charles J. Fickey

[57] ABSTRACT

A novel hair conditioning composition having lathering action and more particularly, it relates to a hair conditioning composition which provides long-lasting conditioning action and cleaner feeling hair.

3 Claims, No Drawings

HAIR CLEANSING CONDITIONER WITH LATHERING ACTION

The present invention relates to a novel hair conditioning composition having lathering action. More particularly, it relates to a hair conditioning composition which provides long-lasting conditioning action and cleaner feeling hair.

A conventional hair conditioning composition, such as a creme rinse conditioner, applied following shampooing, generally comprises a long chain alkyldimethylbenzylammonium chloride compound, the most commonly used being stearyldimethylbenzylammonium chloride. The purpose of the conditioner, particularly the quaternary compound, is to aid in dispersing (neutralizing) the electrostatic (anionic) charges on the hair following shampooing and to otherwise aid in softening the hair and provide manageability. The conventional hair conditioner effectively neutralizes the electrostatic charges, preventing "fly away," but the composition coats the hair shaft. While it leaves the hair feeling soft and manageable, the consumer perceives that something remains on the hair and that it is not completely clean. Moreover, the conditioning action provided is not long lasting.

It is an object of the present invention to provide a hair conditioning composition which has a lathering (foaming) action when applied to the hair; which effectively conditions the hair; which has a long-lasting effect; and which is perceived by the consumer as leaving the hair clean.

These objectives are achieved by the present invention by application of an aqueous pearlescent composition comprising from about 0.5 to 2 percent by weight of a long chain ($C_{12}$ to $C_{20}$) alkyldimethylbenzylammonium chloride compound and from about 3 to 5 percent by weight of a long chain ($C_{10}$ to $C_{18}$) alkyldimethylamine oxide compound. Preferably, the conditioner of the invention is a pearlescent composition comprising from about 1 to 2 percent by weight of stearyldimethylbenzylammonium chloride and from about 3 to 4 percent by weight of lauryldimethylamine oxide.

Alkyldimethylamine oxides have been used to condition the hair. These non-ionic compounds, which behave like cationic materials under acidic conditions, are described by Lang et al., U.S. Pat. No. 3,086,943, as a component of a shampoo containing an anionic or amphoteric detergent. In this composition, the amine oxides are used as foam boosters, since it is known that certain long chain alkyldimethylamine oxides provide lathering action. Sorrentino et al., U.S. Pat. No. 4,007,261, describes a pearlescent hair conditioner composition having a pH between about 5-6. In this composition, the amine oxide may neutralize the anionic charges on the hair following shampooing, but the alkyldimethylamine oxides, having 12 or less carbon atoms, are not good conditioning agents by themselves, and the conditioning effects they provide are not long lasting.

The conditioner of the invention differs in important respects from the prior art conditioners. Thus, the long chain alkyldimethylbenzylammonium chloride compound effectively disperses (neutralizes) the anionic charges on the hair following shampooing. The quaternary compound provides good conditioning action but the molecule is large and does not effectively penetrate the hair shaft in the short contact time. The alkyldimethylamine oxide compound, however, penetrates the hair shaft, rather than merely coating it, thereby leaving the hair feeling cleaner and providing longer-lasting conditioning action. There is evidence suggesting that some of the quaternary compound may also be carried into the hair shaft along with the amine oxide.

The balance between the alkyldimethylbenzylammonium chloride compound and the alkyldimethylamine oxide is important in obtaining the desired long-lasting conditioning effects. Thus, if too much of the quaternary is used, it upsets the equilibrium balance of the ionic composition and prevents the amine oxide from penetrating the hair shaft; if too little quaternary is used, the charge neutralization is incomplete. Similarly, if too much amine oxide is used, the hair is coated, in addition to being penetrated, and the consumer perceives that the hair is not completely clean. If too little amine oxide is used, there is not enough lathering action. This is important, since the lathering action helps to disperse the conditioner uniformly on the hair. However, it is desirable to use as little of the amine oxide in the composition as is needed to achieve the desired effects of the invention. Aesthetically, also, the consumer perceives lathering action to be a cleaning action and, in fact, the hair is left feeling clean and conditioned.

The alkyldimethylbenzylammonium chloride compound used may contain an alkyl group having from 12 to 20 carbon atoms. Stearyl appears to be the optimum chain length and is preferred.

Similarly, the alkyldimethylamine oxide used may contain an alkyl group having 10 to 18 carbon atoms. Lauryldimethylamine oxide is preferred. If the alkyl group contains less than about 12 carbon atoms, the amine oxide tends to become increasingly eye and skin irritating. If the alkyl group contains more than about 18 carbon atoms, lathering action tends to diminish.

The amine oxide functions best at a pH in the range of about 4–6, wherein it takes on a cationic charge which aids in the compound penetrating the hair shaft. Penetration of the quaternary compound into the hair shaft is not efficient because of the size of the molecule. Some is believed carried in by the amine oxide.

The conditioning composition of the invention may contain other commonly used ingredients, which are optional. It may include other conditioning agents, for example, cetyltrimethylammonium chloride; it may contain humectants, softeners, viscosity control compounds, buffers, bacteriocides, dye colors, and the like, without departing from the scope of the invention.

The following composition illustrates the hair conditioner of the invention:

EXAMPLE 1

| Hair Conditioner Composition | Percent |
| --- | --- |
| Lauryldimethylamine oxide (40%) | 10.00 |
| Stearyldimethylbenzylammonium chloride (25%) | 6.00 |
| Glycerin | 5.00 |
| Sorbitan oleate | 2.50 |
| Hydroxyethyl cellulose | 1.00 |
| Fragrance | 1.00 |
| Citric acid | 0.60 |
| Glycolamido stearate | 0.50 |
| Cetyltrimethylammonium chloride (25%) | 0.25 |

| Hair Conditioner Composition -continued | |
|---|---|
| | Percent |
| Water | q.s. to 100 | pH of the composition is 4-6

EXAMPLE 2

In a salon evaluation of the hair conditioner composition of the invention versus a conventional commercial hair conditioner containing essentially stearyldimethylammonium chloride, 20 patrons were subjected to a half-head test. The full hair was first shampooed with an anionic shampoo. The hair was then divided into halves. One side was treated with the composition of the invention and the other side with the commercial product. The conditioned hair was rinsed and set and then evaluated by trained salon operators different from those who treated the hair. The hair was evaluated immediately for body, that is, does the hair feel like more hair, look like more hair; it is less limp, less flat. After 8 hours, the hair was again evaluated to determine whether the hair was less oily and greasy. On a scale of 1-3 (3-being best), the conditioner of the invention showed a +0.5 advantage over the commercial product, which is a statistically significant difference.

EXAMPLE 3

Damaged hair swatches (2 grams) were shampooed with a commercial anionic shampoo containing sodium lauryl sulfate and rinsed. The swatches were then treated with (1) a conventional hair conditioner product containing essentially stearyldimethylammonium chloride and (2) the hair conditioner composition of the present invention, by leaving the conditioner on the hair for one minute. The treated swatches were rinsed thoroughly and then immersed for one minute in the following dye solution, as follows:

PYRAZOL FAST BORDEAU 2BL (5 grams) plus 1.25 grams of glacial acetic acid were dissolved in water to one liter. This solution (100 ml) was diluted to 500 ml with water.

The swatches were then rinsed with water until the water runs clear. The swatches are dried and the intensity of color on each swatch is determined, both visually and instrumentally. The intensity of color is a measure of the amount of quaternary on the hair since the dye reacts with the quaternary to produce dyed hair. Untreated hair is undyed.

In accordance with this test, the intensity of color is significantly greater on hair swatches treated with the composition of the invention versus the conventional hair conditioner.

We claim:

1. An aqueous hair conditioning composition consisting essentially of from about 1 to 2 percent by weight of an alkyl ($C_{12}$ to $C_{20}$) dimethylbenzylammonium chloride compound, from about 3 to 5 percent by weight of an alkyl ($C_{10}$ to $C_{18}$) dimethylamine oxide compound, and about 0.5 percent of an aqueous pearlescent hair conditioning composition comprising glycolamido stearate, said composition having a pH in the range of about 4-6.

2. The composition of claim 1 wherein said alkyldimethylbenzylammonium chloride compound is stearyldimethylbenzylammonium chloride and said alkyldimethylamine oxide is lauryldimethylamine oxide.

3. The composition of claim 2 wherein said lauryldimethyl oxide is used in an amount of from about 3 to 4 percent by weight.

* * * * *